United States Patent
Ogilvie et al.

(10) Patent No.: US 11,020,147 B2
(45) Date of Patent: Jun. 1, 2021

(54) METHOD OF TREATING SCOLIOSIS USING A BIOLOGICAL IMPLANT

(71) Applicant: Predictive Therapeutics, LLC, Salt Lake City, UT (US)

(72) Inventors: James W. Ogilvie, Brighton, UT (US); Kenneth Ward, Salt Lake City, UT (US); Lesa M. Nelson, Park City, UT (US)

(73) Assignee: Predictive Technology Group, Inc., Salt Lake City, UT (US)

( * ) Notice: Subject to any disclaimer, the term of this patent is extended or adjusted under 35 U.S.C. 154(b) by 67 days.

(21) Appl. No.: 15/700,036

(22) Filed: Sep. 8, 2017

(65) Prior Publication Data
US 2018/0008314 A1    Jan. 11, 2018

Related U.S. Application Data

(63) Continuation of application No. 15/488,870, filed on Apr. 17, 2017, now Pat. No. 9,757,152, which is a
(Continued)

(51) Int. Cl.
*A61B 17/88* (2006.01)
*A61B 17/56* (2006.01)
(Continued)

(52) U.S. Cl.
CPC .............. *A61B 17/56* (2013.01); *A61B 17/70* (2013.01); *A61F 2/44* (2013.01); *A61F 5/024* (2013.01);
(Continued)

(58) Field of Classification Search
None
See application file for complete search history.

(56) References Cited

U.S. PATENT DOCUMENTS

| 4,936,848 A | 6/1990 | Bagby ............................ 623/17 |
| 5,158,934 A | 10/1992 | Ammann et al. ............... 514/12 |

(Continued)

FOREIGN PATENT DOCUMENTS

| JP | 2005277195 | 10/1993 | ............... A61N 1/05 |
| JP | 2005169082 | 6/2005 | ............... A61F 2/44 |

(Continued)

OTHER PUBLICATIONS

U.S. Appl. No. 10/976,192, filed Oct. 27, 2004, Campbell et al.
(Continued)

*Primary Examiner* — Sameh R Boles
(74) *Attorney, Agent, or Firm* — GreenbergTraurig, LLP

(57) ABSTRACT

The present invention is a bone growth stimulating and promoting cytokine type biological implant preferably comprising PTH coated with a controlled release biodegradable coating that is implanted preferably in the concave side of a scoliotically curved spine in combination with a bone growth inhibiting type biological implant preferably comprising methotrexate or like anti-metabolite coated with a controlled release biodegradable coating that is implanted preferably in the convex side of a scoliotically curved spine. The insertion of the biological implant is highly non-invasion, especially as compared to more conventional spine surgical methods, and the biological implant does not decrease spinal mobility or spinal range of motion.

23 Claims, 2 Drawing Sheets

Related U.S. Application Data continuation of application No. 15/186,914, filed on Jun. 20, 2016, now Pat. No. 9,623,152, which is a continuation of application No. 14/170,691, filed on Feb. 3, 2014, now Pat. No. 9,370,431, which is a continuation-in-part of application No. 13/357,800, filed on Jan. 25, 2012, now Pat. No. 8,641,738, which is a continuation-in-part of application No. 12/341,289, filed on Dec. 22, 2008, now Pat. No. 8,123,787, said application No. 13/357,800 is a continuation-in-part of application No. 11/259,941, filed on Oct. 26, 2005, now abandoned, and a continuation-in-part of application No. 11/968,046, filed on Dec. 31, 2007, now abandoned, which is a continuation of application No. PCT/US2007/072785, filed on Jul. 3, 2007.

(60) Provisional application No. 61/073,119, filed on Jun. 17, 2008, provisional application No. 61/082,503, filed on Jul. 21, 2008, provisional application No. 60/622,999, filed on Oct. 28, 2004, provisional application No. 60/806,498, filed on Jul. 3, 2006, provisional application No. 60/825,260, filed on Sep. 11, 2006.

(51) Int. Cl.
*A61L 27/58* (2006.01)
*A61B 17/70* (2006.01)
*A61L 27/54* (2006.01)
*A61F 2/44* (2006.01)
*A61F 5/02* (2006.01)
*A61B 17/00* (2006.01)
*A61B 17/68* (2006.01)

(52) U.S. Cl.
CPC .............. *A61L 27/54* (2013.01); *A61L 27/58* (2013.01); *A61B 2017/00004* (2013.01); *A61B 2017/00893* (2013.01); *A61B 2017/564* (2013.01); *A61B 2017/681* (2013.01); *A61F 2002/448* (2013.01); *A61F 2210/0004* (2013.01); *A61F 2250/0067* (2013.01); *A61L 2300/412* (2013.01); *A61L 2300/414* (2013.01); *A61L 2300/416* (2013.01); *A61L 2300/43* (2013.01); *A61L 2300/45* (2013.01); *A61L 2300/604* (2013.01); *A61L 2430/38* (2013.01)

(56) References Cited

U.S. PATENT DOCUMENTS

| | | | |
|---|---|---|---|
| 5,263,985 A | 11/1993 | Bao et al. | 623/16 |
| 5,409,896 A | 4/1995 | Ammann et al. | 514/13 |
| 5,604,204 A | 2/1997 | Ammann et al. | 514/12 |
| 5,672,175 A | 9/1997 | Martin | 606/61 |
| 6,322,786 B1 | 11/2001 | Anderson | 424/115 |
| 6,558,390 B2 | 5/2003 | Cragg | 606/80 |
| 7,108,862 B2 | 9/2006 | Remington et al. | 424/426 |
| 7,206,638 B2 | 4/2007 | Dodge et al. | 607/43 |
| 7,309,338 B2 | 12/2007 | Cragg | 606/80 |
| 7,537,782 B2 | 5/2009 | Calhoun et al. | 424/426 |
| 7,574,261 B2 | 8/2009 | Dodge et al. | 607/43 |
| 7,794,463 B2 | 9/2010 | Cragg | 606/80 |
| 7,837,735 B2 | 11/2010 | Malone | 623/17.16 |
| 7,967,767 B2 | 6/2011 | Ogilvie | |
| 8,017,144 B2 | 9/2011 | Dumont et al. | 424/426 |
| 8,088,402 B2 | 1/2012 | Remington et al. | 424/423 |
| 8,092,541 B2 | 1/2012 | Peckham | 623/17.16 |
| 8,123,787 B2 | 2/2012 | Ogilvie et al. | |
| 8,641,738 B1 | 2/2014 | Ogilvie et al. | |
| 9,149,499 B1 | 10/2015 | Robinson | |
| 9,161,941 B2 | 10/2015 | Robinson | |
| 9,370,431 B2 | 6/2016 | Ogilvie et al. | |
| 9,623,152 B2 | 4/2017 | Ogilvie et al. | |
| 9,757,152 B2 | 9/2017 | Ogilvie et al. | |
| 2001/0049527 A1 | 12/2001 | Cragg | 606/61 |
| 2002/0102614 A1 | 8/2002 | Davis et al. | 435/7.1 |
| 2003/0185874 A1 | 10/2003 | Calhoun et al. | 424/426 |
| 2004/0006125 A1 | 1/2004 | Remington et al. | 514/423 |
| 2004/0199219 A1 | 10/2004 | Dodge et al. | 607/51 |
| 2004/0225360 A1 | 11/2004 | Malone | 623/17.11 |
| 2005/0015002 A1 | 1/2005 | Dixon et al. | 600/407 |
| 2005/0015154 A1 | 1/2005 | Lindsey et al. | 623/23.46 |
| 2005/0033427 A1 | 2/2005 | Freilich et al. | 623/16.11 |
| 2005/0203511 A1 | 9/2005 | Wilson-MacDonald et al. | 606/61 |
| 2005/0249697 A1 | 11/2005 | Uhrich et al. | 424/78.37 |
| 2006/0155279 A1 | 7/2006 | Ogilvie | 606/61 |
| 2006/0212088 A1 | 9/2006 | Dodge et al. | 607/43 |
| 2006/0233853 A1 | 10/2006 | Remington et al. | 424/422 |
| 2007/0083265 A1 | 4/2007 | Malone | 623/17.11 |
| 2008/0091199 A1 | 4/2008 | Cragg | 606/60 |
| 2008/0241211 A1 | 10/2008 | Han et al. | 424/423 |
| 2009/0035768 A1 | 2/2009 | Nelson et al. | 435/6 |
| 2009/0035769 A1 | 2/2009 | Nelson et al. | |
| 2009/0035772 A1 | 2/2009 | Nelson et al. | |
| 2009/0036988 A1 | 2/2009 | Peckham | 623/17.16 |
| 2009/0105822 A1 | 4/2009 | Ogilvie | 623/17.11 |
| 2009/0169595 A1 | 7/2009 | Dumont et al. | 424/423 |
| 2011/0295369 A9 | 12/2011 | Ogilvie | 623/17.11 |
| 2016/0022696 A1 | 1/2016 | Robinson | |
| 2017/0112881 A1 | 4/2017 | Robinson | |

FOREIGN PATENT DOCUMENTS

| | | | |
|---|---|---|---|
| KR | 1020040031783 | 4/2004 | A61K 33/06 |
| KR | 1020040039802 | 5/2004 | A61B 17/86 |
| KR | 1020040062977 | 7/2004 | A61K 31/44 |
| WO | WO1996/00592 | 1/1996 | A61L 27/00 |
| WO | WO2003/045351 | 6/2003 | A61K 9/00 |
| WO | WO2006/049797 | 5/2006 | A61F 2/28 |
| WO | WO2008006001 | 1/2008 | |
| WO | WO2008/076671 | 6/2008 | A61L 27/34 |
| WO | WO-2014189836 A1 | 11/2014 | |

OTHER PUBLICATIONS

U.S. Appl. No. 11/610,957, filed Dec. 14, 2006, McKay.
U.S. Appl. No. 60/337,255, filed Nov. 30, 2001, Dumont et al.
U.S. Appl. No. 60/622,999, filed Oct. 28, 2004, Ogilvie.
U.S. Appl. No. 60/806,498, filed Jul. 3, 2006, Nelson et al.
U.S. Appl. No. 60/825,260, filed Sep. 11, 2006, Nelson et al.
U.S. Appl. No. 61/073,119, filed Jun. 17, 2008, Ogilvie.
U.S. Appl. No. 61/082,503, filed Jul. 21, 2008, Nelson et al.
Braun et al., Twelve DNA Markers Accurately Assess Risk of Progression in AIS, SRS 42$^{nd}$ Annual Meeting Presentations, p. 94, Paper #90, Sep. 2007.
Inoue et al., Association Between Estrogen Receptor Gene Polymorphisms and Curve Severity of Idiopathic Scoliosis, 2002 Spine vol. 27, No. 21, pp. 2357-2362.
Tang et al., A Relook Into the Association of the Estrogen Receptor Gene (PvuII, XbaI) and Adolescent Idiopathic Scoliosis, 2006 Spine vol. 31, No. 21, pp. 2463-2468.
Co-pending U.S. Appl. No. 60/825,249, filed Sep. 11, 2006.
Co-pending U.S. Appl. No. 60/862,276, filed Oct. 20, 2006.
U.S. Appl. No. 12/341,289 Notice of Allowance dated Nov. 7, 2011.
U.S. Appl. No. 12/341,289 Office Action dated Apr. 12, 2010.
U.S. Appl. No. 12/341,289 Office Action dated Aug. 6, 2010.
U.S. Appl. No. 12/341,289 Office Action dated Dec. 30, 2010.
U.S. Appl. No. 12/341,289 Office Action dated Jul. 24, 2009.
U.S. Appl. No. 12/341,289 Office Action dated Mar. 11, 2009.
U.S. Appl. No. 12/341,289 Office Action dated May 20, 2009.
U.S. Appl. No. 12/341,289 Office Action dated Nov. 17, 2009.
U.S. Appl. No. 13/357,800 Office Action dated Sep. 17, 2013.
U.S. Appl. No. 14/170,691 Office Action dated Feb. 4, 2015.
U.S. Appl. No. 14/170,691 Office Action dated Jan. 22, 2015.

(56) References Cited

OTHER PUBLICATIONS

U.S. Appl. No. 15/186,914 Notice of Allowance dated Dec. 15, 2016.
U.S. Appl. No. 15/186,914 Office Action dated Sep. 8, 2016.
U.S. Appl. No. 15/488,870 Notice of Allowance dated Aug. 3, 2017.

METHOD OF TREATING SCOLIOSIS USING A BIOLOGICAL IMPLANT

CROSS REFERENCE TO RELATED APPLICATIONS

This nonprovisional utility application is a continuation of and claims the benefit under 35 USC §120 to U.S. application Ser. No. 15/488,870 filed Apr. 17, 2017 and scheduled to issue as U.S. Pat. No. 9,757,152 on Sep. 12, 2017 which is a continuation of and claims the benefit under 35 USC §120 to U.S. application Ser. No. 15/186,914 filed Jun. 20, 2016 and since issued as U.S. Pat. No. 9,623,152 on Apr. 18, 2017 which is a continuation of and claims the benefit under 35 USC §120 to U.S. application Ser. No. 14/170,691 filed Feb. 3, 2014 and since issued as U.S. Pat. No. 9,370,431 on Jun. 21, 2016 which is a continuation-in-part of and claims the benefit under 35 USC §120 to U.S. application Ser. No. 13/357,800 filed Jan. 25, 2012 and since issued as U.S. Pat. No. 8,641,738 on Feb. 4, 2014 which is a continuation-in-part of and claims the benefit under 35 USC §120 to U.S. application Ser. No. 12/341,289 filed Dec. 22, 2008 and since issued as U.S. Pat. No. 8,123,787 on Feb. 28, 2012 which claims the benefit under 35 USC §119(e) of U.S. Provisional Application No. 61/073,119, filed Jun. 17, 2008 and of U.S. Provisional Patent Application No. 61/082,503, filed Jul. 21, 2008, and is a continuation-in-part of and claims the benefit under 35 USC §120 to co-pending U.S. application Ser. No. 11/259,941 filed Oct. 26, 2005 which claims the benefit under 35 USC §119(e) of U.S. Provisional Application No. 60/622,999, filed Oct. 28, 2004, and is a continuation-in-part of and claims the benefit under 35 USC §120 to co-pending U.S. application Ser. No. 11/968,046 filed Dec. 31, 2007 and is a continuation of and claims the benefit under 35 USC §365(c) of International Patent Application No. PCT/US2007/072785 with an international filing date of Jul. 3, 2007 which claims the benefit under 35 USC §119(e) of U.S. Provisional Application No. 60/806,498, filed Jul. 3, 2006 and of U.S. Provisional Patent Application No. 60/825,260, filed Sep. 11, 2006, all of which are incorporated, in their entirety, by this reference.

FIELD OF THE INVENTION

The present invention relates to the management of bone growth, and more especially management of bone growth to correct for skeletal deformities such as scoliosis through the selective use of biological implants.

BACKGROUND OF THE INVENTION

Scoliosis, a medical condition in humans typically characterized by the side-to-side or lateral curvature of the spine, is a common problem affecting more than 2 percent of the US population. Further other related skeletal problems are also common in the human population. Many inventions have been directed to therapeutics for the prevention and correction of scoliosis and like conditions. Such therapeutics include for instance corrective bracing, corrective surgery and certain exercise routines. Certain instances of such therapeutics have shown greater effectiveness than others. In the case of corrective surgery, such therapeutic may prove highly effective in correcting scoliosis but typically is relatively invasive and potentially traumatic to the patient, and may result in the loss of mobility and range of motion of the spine. Accordingly, there exists a need to for a preventative and corrective scoliosis therapeutic that is highly minimally invasive and does not reduce the patient's mobility and range of motion.

SUMMARY OF THE INVENTION

The present invention therefore is a method and apparatus for bone growth management using biological implants. In an embodiment of the invention, a first implant defines a bone growth stimulating and promoting cytokine type biological implant such as Parathyroid hormone (PTH) having a controlled release or controlled time dissolvable biodegradable coating, and a second implant defines a bone growth inhibiting type biological implant such as a composition that includes as at least a portion thereof methotrexate or like anti-metabolite and having a controlled release or controlled time dissolvable biodegradable coating. The first implant is preferably inserted between vertebra, near a growth plate, on the concave side of a scoliotically curved spine by means of inserting the tip of a trocar into the desired area of the spine, and passing the implant through the trocar and into the desired area of the spine of a patient. The second implant is preferably inserted between vertebra, near a growth plate, on the convex side of a scoliotically curved spine by means of inserting the tip of a trocar into the desired area of the spine, and passing the implant through the trocar and into the desired area of the spine of a patient. After implant insertion and over the course of time, the implants dissolve releasing the bone growth simulating cytokine and the bone growth inhibiting composition to the vertebra. In response, the vertebra grows a greater amount on a concave side of the spine than on a convex side of the spine. This asymmetric growth of the spine over time causes the spine to transition from a substantially scoliotically curved configuration to a substantially non-scoliotically curved configuration.

DESCRIPTION OF DRAWINGS

In order that the advantages of the invention will be readily understood, a more particular description of the invention briefly described above will be rendered by reference to specific embodiments that are illustrated in the appended drawings. Understanding that these drawings depict only typical embodiments of the invention and are not therefore to be considered to be limiting of its scope, the invention will be described and explained with additional specificity and detail through the use of the accompanying drawings, in which.

DETAILED DESCRIPTION OF THE INVENTION

Figure 1:
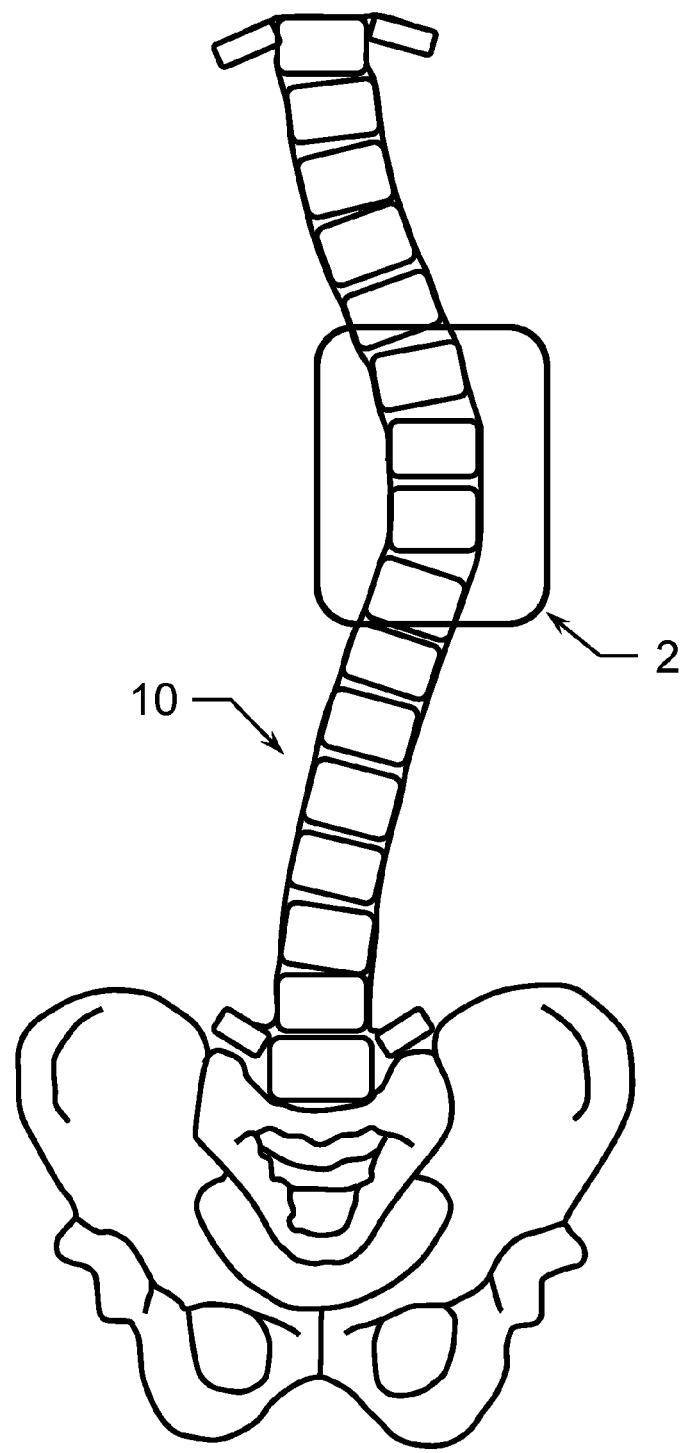
FIG. 1 is a substantially orthographic anterior/posterior schematic view of a scoliotic spine.
Figure 2:
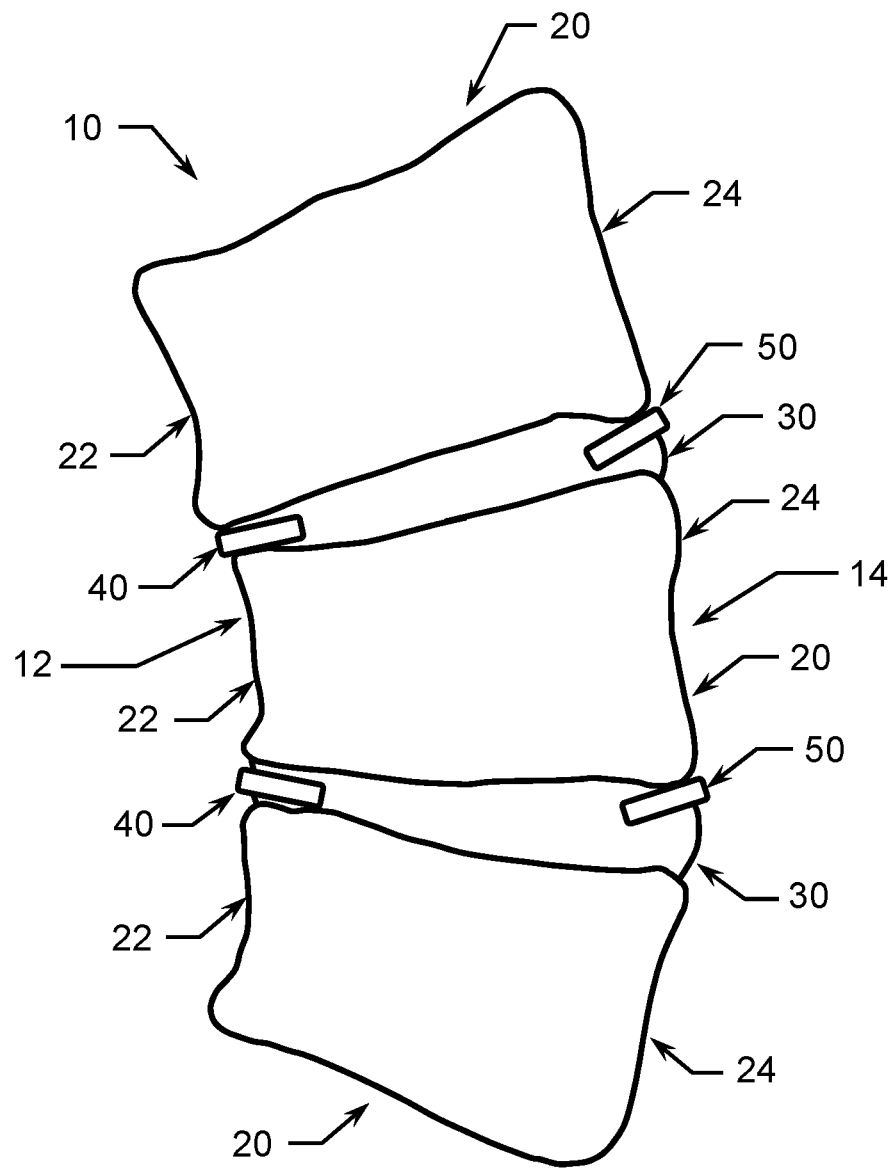
FIG. 2 is a close-up schematic view of a portion of the spine shown in FIG. 1.

Reference throughout this specification to "one embodiment," "an embodiment," or similar language means that a particular feature, structure, or characteristic described in connection with the embodiment is included in at least one embodiment of the present invention. Thus, appearances of the phrases "in one embodiment," "in an embodiment," and similar language throughout this specification may, but do not necessarily, all refer to the same embodiment.

Furthermore, the described features, structures, or characteristics of the invention may be combined in any suitable manner in one or more embodiments. In the following description, numerous specific details are included to provide a thorough understanding of embodiments of the invention. One skilled in the relevant art will recognize, however, that the invention can be practiced without one or more of the specific details, or with other methods, components, materials, and so forth. In other instances, well-known structures, materials, or operations are not shown or described in detail to avoid obscuring aspects of the invention.

It is known that growth of the physeal plate results in longitudinal growth of long bones. In the spine, increase in height of vertebral bodies is accomplished through growth of the cartilaginous endplate. Growth of the physeal plate is influenced by both mechanical factors and signaling molecules. Stimulation of physeal chondrocytes growth is controlled through a complex interaction of local and systemic pathways. Many cytokines (a category of signaling proteins) have an anabolic effect of growth plate cartilage.

Specifically it is known that Parathyroid hormone (PTH) stimulates physeal chondrocytes. The overall effect of PTH on the growth plate chondrocyte appears to be a stimulation of proteoglycan synthesis that is mediated by the degradation products of membrane phosphoinositides.

It is known that Fibroblast growth factors can stimulate growth of the physeal plate. In chick growth plate chondrocytes tritiated thymidine incorporation was increased 11-fold by fibroblast growth factor (10 ng/ml) and 3.5 by TGF-beta. Studies have identified FGF18 as a selective ligand for FGFR3 in limb bud mesenchymal cells, which suppressed proliferation and promoted their differentiation and production of cartilage matrix. Research work has identified FGF18 and FGFR3 as potential molecular targets for intervention in tissue engineering aimed at cartilage repair and regeneration of damaged cartilage.

Furthermore, it is know that androgens have an anabolic effect, and it is known that Insulin-like Growth Factors (IGF), Estrogens, and Transforming Growth Factors (TGF), all stimulate growth. Calcium metabolism has an influence on growth plate activity. Inorganic phosphate may act as a signaling molecule in the regulation of bone formation. All of the above listed cytokines may be incorporated in the form of a biological implant.

Furthermore, it is known that methotrexate or like anti-metabolites function to inhibit bone growth. Methotrexate or like anti-metabolite may be incorporated in the form of a biological implant.

The biological implant is preferably coated with a timed release or time dissolvable biodegradable coating. Such coatings are commercially available for instance from the SurModics Corporation and sold under various trademarked names such as SynBiosys, Eureka and PolyActive. The implant may be shaped for instance in the form of a cylinder with rounded or hemispherically shaped ends. Alternatively, the implant may be preformed to adapt to a particular implantation target site, for instance a surface of the implant may be shaped to form to the shape of a portion of a vertebra. Further alternatively, the implant may be somewhat compliant so as to be at least partially pressed into a shaped that conforms to a target site such as to the shape of a portion of a vertebra.

In order to facilitate the understanding of the present invention in reviewing the drawings accompanying the specification, a feature list is provided below. It is noted that like features are like numbered throughout all of the figures.

| FEATURE TABLE | |
|---|---|
| # | Feature |
| 10 | Scoliotic vertebrae or spine |
| 12 | Scoliotic vertebrae concave side |
| 14 | Scoliotic vertebrae convex side |
| 20 | Scoliotic vertebra |
| 22 | Scoliotic vertebra concave side |
| 24 | Scoliotic vertebra convex side |
| 30 | Spinal disk |
| 40 | Biological implant - growth promoting |
| 50 | Biological implant - bone growth inhibiting |

Referring now to the drawings, the invention is a first bone growth stimulating and promoting cytokine type biological implant 40 comprising PTH coated with a controlled release biodegradable coating that is implanted preferably in close proximity to a concave side 12 of a scoliotically curved spine 10, and a second bone growth inhibiting type biological implant 50 comprising a bone growth inhibiting composition such as methotrexate coated with a controlled release biodegradable coating that is implanted preferably in close proximity to a convex side 14 of a scoliotically curved spine 10. More specifically, implant 40 is preferably implanted between a concave side 22 of a first scoliotic vertebra 20 and a concave side 22 of a second scoliotic vertebra 20, so as to be in near proximity to at least one growth plate of vertebra 20 and so as to be in near proximity to disk 30 and implant 50 is preferably implanted between a convex side 24 of a first scoliotic vertebra 20 and a concave side 24 of a second scoliotic vertebra 20, so as to be in near proximity to at least one growth plate of vertebra 20 and so as to be in near proximity to disk 30. Alternatively, it is noted however, that rather than both bone growth promoting implant 40 and bone growth inhibiting implant 50 being used in combination, bone growth promoting implant 40 may be used without bone growth inhibiting implant 50, and bone growth inhibiting implant 50 may be used without bone growth promoting implant 40. First biological implant 40 is preferably inserted between a first vertebra 20 and a second vertebra 20 on concave side 12 of scoliotically curved spine 10 by means of inserting the tip of a trocar into the desired area of concave side 12 of scoliotically curved spine 10, and passing implant 40 through the trocar and into the desired area of scoliotically curved spine 10 of a patient. Second biological implant 50 is preferably inserted between a first vertebra 20 and a second vertebra 20 on convex side 14 of scoliotically curved spine 10 by means of inserting the tip of a trocar into the desired area of convex side 14 of scoliotically curved spine 10, and passing implant 50 through the trocar and into the desired area of scoliotically curved spine 10 of a patient. Such insertion of biological implants 40 and 50 is highly non-invasive, requiring only small incisions, as compared to more conventional spine surgical methods which require large and invasive surgical cuts. Further, the insertion of such biological implants 40 and 50 does not decrease spinal mobility or spinal range of motion. Over the course of time, the implants 40 and 50 dissolve releasing the bone growth simulating cytokine and/or the bone growth inhibiting anti-metabolite or functional equivalent to vertebrae 10. In response to such implantation, vertebrae 10 grows a greater amount on concave side 12 of the vertebrae 10 than on convex side 14 of vertebrae 10. The asymmetric growth of vertebrae 10 over time causes vertebrae 10 to transition from a substantially scoliotically curved configuration to a substantially non-scoliotically curved configuration.

It is noted that the disclosed invention is preferably practiced in combination with a screening test that screens patients for a predisposition to scoliosis, and more especially, that screens scoliosis patients for a predisposition to scoliosis curve progression. Such scoliosis and scoliosis curve progression screening is disclosed in U.S. patent applications 60/806,498, 60/825,260, 60/825,249, 60/862,276, Ser. Nos. 11/968,046, 11/968,074, 12/024,495, and 61/082,503 the whole of which are incorporated herein by reference. Such screening tests specifically provide novel SNPs in genetic sequences involved in methods of identifying individuals who have an altered risk of developing scoliosis or for developing a progressive scoliosis curve based on the presence of a SNP(s) so disclosed and methods of identifying individuals who are more or less likely to respond to a treatment. Such SNPs can be associated with either an increased or decreased likelihood or risk of developing scoliosis or scoliosis progressive. Thus the term "altered" may be used herein to encompass either of the two possibilities (e.g. an increased or a decreased risk/likelihood). Thus by means of employing such screening, the method and apparatus for bone growth management using a biological implant as disclosed herein, is preferably only practiced on those patients who are determined to be at risk for scoliosis curve development or progression.

It is noted that the disclosed invention may further practiced in combination with applying a brace to the patient. An exemplary brace for the treatment of scoliosis preferably used in combination with the method and apparatus for bone growth management using a biological implant as disclosed herein is disclosed in U.S. patent application Ser. No. 12/145,959 which since issued as U.S. Pat. No. 7,967,767 on Jun. 28, 2011, the whole of which is incorporated herein by reference.

It is noted that the disclosed invention may further be practiced in combination with preferably minimally invasive non-biological implants for the correction of a scoliotically curved spine. An exemplary non-biological implant for the treatment of scoliosis preferably used in combination with the method and apparatus for bone growth management using a biological implant as disclosed herein is disclosed in U.S. patent application Ser. No. 11/259,941 which the current application is a continuation-in-part thereof, and the whole of which is incorporated herein by reference.

It is noted that in an alternative to a biological implant that completely dissolves over time, the implant of the present invention may be a permanent implant. It is also noted that in an additional embodiment, the implant may alternatively be placed on a side of the disc or in the general vicinity of the concave or convex side of the spine.

The present invention relates to novel genetic markers associated with scoliosis, risk of developing scoliosis and risk of scoliosis curve progression, and methods and materials for determining whether a human subject has scoliosis, is at risk of developing scoliosis or is at risk of scoliosis curve progression.

Scoliosis in one instance refers to adolescent idiopathic scoliosis (AIS). In another instance scoliosis refers to either congenital, juvenile, syndromic or any other scoliosis condition. For the purpose of this invention the term scoliosis is used to describe any of these conditions.

The contribution or association of particular SNPs and/or SNP haplotypes with scoliosis phenotypes, such as AIS, enables the SNPs of the present invention to be used to develop superior diagnostic tests capable of identifying individuals who express a detectable trait, such as scoliosis, as the result of a specific genotype, or individuals whose genotype places them at an increased or decreased risk of developing a detectable trait at a subsequent time as compared to individuals who do not have that genotype. For example, the presence of a single SNP known to correlate with scoliosis might indicate an odds ratio of 1.5 that an individual has or is at risk of developing scoliosis, whereas detection of five SNPs, each of which correlates with scoliosis, might indicate an odds ratio of 9.5 that an individual has or is at risk of developing scoliosis. To further increase the accuracy of diagnosis or predisposition screening, analysis of the SNPs of the present invention can be combined with that of other polymorphisms or other risk factors of scoliosis, such as Cobb angle, Risser sign, gender and age.

It shall be noted that the invention disclosed herein is highly useful in segregating and treating scoliotic patients. For instance, the invention is useful in segregating patients into two categories, namely those scoliotic patients whose scoliotic spine curvature will increase from those whose scoliotic spine curvature will not increase. Furthermore, the invention is useful in appropriately treating such segregated patients. For instance in patients whose scoliotic spine curvature will increase, a therapeutic such as implanting a biological implant into the patient, performing spinal surgery on the patient, applying a brace to the patient, continuing the use of a brace on the patient, taking a spinal X-ray of the patient, continuing ongoing periodic spinal X-rays of the patient, and monitoring spine curve progression of the patient is administered whereas in patients whose scoliotic spine curvature will not increase, a therapeutic such as the cancelation of a contemplated implantation of a biological implant into the patient, the cancelation of contemplated spinal surgery of the patient, the prevention of the application of a brace to the patient, the cancelation of continued use of a brace on the patient, the prevention of the taking of a spinal X-ray of the patient, the cancelation of ongoing periodic spinal X-rays of the patient, and the cancelation of monitoring of spine curve progression of the patient is administered.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. A method of treating a subject in need thereof comprising:
   contacting a therapeutic to a site of a subject in need thereof to treat a genetically inherited adolescent female dominant disease comprising an adolescent idiopathic scoliosis (AIS),
   wherein a genetically inherited adolescent female dominant disease altered risk associated biological marker comprising a SNP is present in a sample of said subject in need thereof, and
   wherein said therapeutic comprises an implant and stimulates or inhibits tissue growth at said site.

2. The method of claim 1, wherein said therapeutic comprises a biological component.

3. The method of claim 1, wherein said genetically inherited adolescent female dominant disease altered risk associated biological marker is of a minor allele.

4. The method of claim 1, wherein said contacting comprises at least one of: providing a biological component to said subject in need thereof, performing a spinal surgery on said subject in need thereof, contacting a brace to said subject in need thereof, continuing contact of a brace on said subject in need thereof, taking a spinal X-ray of said subject in need thereof, continuing periodic spinal X-rays of said subject in need thereof, and monitoring a spine curve progression of said subject in need thereof.

5. The method of claim 4, wherein said contacting comprises providing said biological component to said subject in need thereof, and wherein said biological component comprises at least one of: (a) a dissolvable bone growth stimulant coated with a dissolvable coating and (b) a dissolvable bone growth inhibitor coated with a dissolvable coating.

6. The method of claim 5, wherein said biological component comprises said dissolvable bone growth stimulant, and wherein said bone growth stimulant comprises at least one of: a Parathyroid hormone, a Fibroblast growth factor, an androgen, an Insulin-like Growth Factor, an Estrogen, a Transforming Growth Factor, an inorganic phosphate, or any combination thereof.

7. The method of claim 5, wherein said biological component comprises said dissolvable bone growth inhibitor, and wherein said bone growth inhibitor comprises methotrexate.

8. The method of claim 4, wherein said contacting comprises providing said biological component to said subject in need thereof, wherein at least a portion of a spine of said subject in need thereof comprises a curvature, and wherein at least one bone growth promoting portion of said biological component is contacted proximate a concave side of said curvature of said portion of said spine, and wherein at least one bone growth inhibiting portion of said biological component is contacted proximate a convex side of said curvature of said portion of said spine.

9. The method of claim 1, wherein said genetically inherited adolescent female dominant disease altered risk associated biological marker is detected by a screening test.

10. The method of claim 1, wherein a presence of said genetically inherited adolescent female dominant disease altered risk associated biological marker in said sample of said subject in need thereof is known to a person prescribing said therapeutic.

11. A method of treating a subject in need thereof comprising:
contacting a therapeutic to a subject in need thereof to treat a genetically inherited adolescent female dominant disease comprising an adolescent idiopathic scoliosis (AIS),
wherein a genetically inherited adolescent female dominant disease altered risk associated biological marker comprising a SNP is present in a sample of said subject in need thereof, and
wherein said therapeutic comprises an implant and does not prevent or delay a progression of a spinal deformation in said subject in need thereof.

12. The method of claim 11, wherein said resistance to said spine deformation comprises a resistance to an increased scoliotic spine curvature.

13. The method of claim 11, wherein said genetically inherited adolescent female dominant disease altered risk associated marker is of a minor allele, wherein said genetically inherited adolescent female dominant disease altered risk associated biological marker comprises a SNP.

14. The method of claim 11, wherein said therapeutic does not comprise a brace.

15. The method of claim 14, further comprising cancelling a recurring contacting of said therapeutic to said subject in need thereof.

16. A method of treating a subject in need thereof comprising:
contacting at least one of:
(i) a therapeutic that comprises an implant and stimulates or inhibits a tissue growth; and
(ii) a therapeutic that comprises an implant and does not prevent or delay a progression of a spinal deformation
to a subject in need thereof to treat a genetically inherited adolescent female dominant disease comprising an adolescent idiopathic scoliosis (AIS),
wherein a genetically inherited adolescent female dominant disease altered risk associated biological marker comprising a SNP is present in a sample of said subject in need thereof.

17. The method of claim 16, wherein said resistance to said spine deformation comprises a resistance to an increased scoliotic spine curvature.

18. The method of claim 16, wherein said genetically inherited adolescent female dominant disease altered risk associated biological marker is of a minor allele.

19. The method of claim 16, wherein said contacting comprises at least one of: contacting a biological component to said site of said subject in need thereof, performing a spinal surgery on said subject in need thereof, contacting a brace to said subject in need thereof, continuing contact of a brace on said subject in need thereof, taking a spinal X-ray of said subject in need thereof, continuing periodic spinal X-rays of said subject in need thereof, and monitoring a spine curve progression of said subject in need thereof.

20. The method of claim 19, wherein said contacting comprises providing said biological to said subject in need thereof, and wherein said biological component comprises at least one of: (a) a dissolvable bone growth stimulant coated with a dissolvable coating and (b) a dissolvable bone growth inhibitor coated with a dissolvable coating.

21. The method of claim 20, wherein said biological component comprises said dissolvable bone growth stimulant, and wherein said bone growth stimulant comprises at least one of: a Parathyroid hormone, a Fibroblast growth factor, an androgen, an Insulin-like Growth Factor, an Estrogen, a Transforming Growth Factor, an inorganic phosphate, or any combination thereof.

22. The method of claim 20, wherein at least a portion of a spine of said subject in need thereof comprises a curvature, and wherein at least one bone growth promoting portion of said biological component is contacted proximate a concave side of said curvature of said portion of said spine, and wherein at least one bone growth inhibiting portion of said biological component is contacted proximate a convex side of said curvature of said portion of said spine.

23. The method of claim 20, wherein said biological component comprises said dissolvable bone growth inhibitor, and wherein said bone growth inhibitor comprises methotrexate.

* * * * *